(12) United States Patent
Lotan

(10) Patent No.: US 7,081,247 B2
(45) Date of Patent: Jul. 25, 2006

(54) COMPOSITION AND METHOD FOR INHIBITING POLAR CAPSULE DISCHARGE AND PROTECTING A SUBJECT FROM NEMATOCYST STING

(75) Inventor: Amit Lotan, Jordon Valley (IL)

(73) Assignee: Nidaria Technology Ltd., Zemach (IL)

( * ) Notice: Subject to any disclaimer, the term of this patent is extended or adjusted under 35 U.S.C. 154(b) by 106 days.

(21) Appl. No.: 10/150,092

(22) Filed: May 20, 2002

(65) Prior Publication Data

US 2003/0215404 A1 Nov. 20, 2003

(51) Int. Cl.
*A01N 25/00* (2006.01)
*A61K 8/18* (2006.01)
*A61K 9/00* (2006.01)
*A61K 6/00* (2006.01)
*A61K 33/00* (2006.01)

(52) U.S. Cl. .................. 424/405; 424/59; 424/400; 424/401; 424/600; 424/650

(58) Field of Classification Search .............. 424/400, 424/401, 59, 405, 600, 650
See application file for complete search history.

(56) References Cited

U.S. PATENT DOCUMENTS

| | | | |
|---|---|---|---|
| 4,234,566 A | | 11/1980 | Packman et al. |
| 4,529,593 A | * | 7/1985 | Warrell et al. .............. 424/650 |
| 4,596,710 A | * | 6/1986 | Collery ........................ 424/650 |
| 4,847,083 A | | 7/1989 | Clark |
| 4,873,265 A | | 10/1989 | Blackman |
| 4,917,889 A | | 4/1990 | Carty et al. |
| 4,929,619 A | | 5/1990 | Blackman |
| 5,175,006 A | * | 12/1992 | Matkovic et al. ........... 424/650 |
| 5,202,130 A | | 4/1993 | Grant et al. |
| 5,756,107 A | | 5/1998 | Hahn et al. |
| 5,851,556 A | | 12/1998 | Breton et al. |
| 5,866,168 A | | 2/1999 | De Lacharriere et al. |
| 5,900,257 A | * | 5/1999 | Breton et al. ............... 424/639 |
| 6,277,388 B1 | * | 8/2001 | Chevalier .................. 424/401 |

FOREIGN PATENT DOCUMENTS

| | | |
|---|---|---|
| GB | 2110534 | 6/1983 |
| WO | WO 94/17779 | 8/1994 |

OTHER PUBLICATIONS

Salleo et al., "Gadolinium is a powerful blocker of the activation of nematocytes of *Pelagia noctiluca*", (1994) J. Exp. Biol. 187, 201-206.*

Santoro et al., "The discharge of in situ nematocysts of the acontia of Aiptasia Mutabilis is a Ca2+-induced response", (1991) J. Exp. Biol. 156, 173-185.*

Hidaka et al. "Effects of Cations on the Volume and Elemental Composition of Nematocysts isolated from Acontia of the Sea Anemone *Calliactis polypus*", Feb. 1993, Biol. Bull. 184:97-104.

Lubbock et al., "Novel Role of Calcium in Exocystosis: Mechanism of Nematocyst Discharge as shown by X-ray Microanalysis", Proc. Natl. Acad. Sci. USA, vol. 78, No. 6, Jun. 1981, pp. 3624-2628.

Russell et al., "Clinical Articles Seabather's Eruption or Sea Lice: New Findings and Clinical Implications", downloaded from www.fau.edu/safe/sea-lice, 1995.

Salleo et al., "Gadolinium is a Powerful Blocker of the Activation of Nematocytes of *Pelagia noctiluca*", J. Exp. Biol. 187, 1994, pp. 201-206.

Santoro et al., The Discharge of *In Situ* Nematocysts of the Acontia of *Aiptasia mutabilis* is a $Ca^{2+}$-Induced Response, J. Exp. Biol. 156, 1991, pp. 173-185.

* cited by examiner

*Primary Examiner*—Sreeni Padmanabhan
*Assistant Examiner*—Marina Lamm
(74) *Attorney, Agent, or Firm*—Pearl Cohen Zedek Latzer, LLP

(57) ABSTRACT

The present invention provides compositions comprising at least one cation selected from the group consisting of $Ga^{+3}$ and $La^{+3}$, that effectively inhibit the discharge of nematocysts or polar capsules. The compositions described herein are effective at inhibiting nematocyst or polar capsule discharge when applied topically prior to exposure to nematocysts. The present invention further provides methods for inhibiting the discharge of nematocysts or polar capsules, comprising applying to the skin of a subject prior to contact with the nematocyst or polar capsule a compositions comprising at least one cation selected from the group consisting of $Ga^{+3}$ and $La^{+3}$. Thus, the present invention provides protection for swimmers, divers and fishermen, from nematocysts or polar capsules discharged from stinging marine organisms such as *Cnidaria* and *Myxozoa*.

27 Claims, 2 Drawing Sheets

COMPOSITION AND METHOD FOR INHIBITING POLAR CAPSULE DISCHARGE AND PROTECTING A SUBJECT FROM NEMATOCYST STING

FIELD OF THE INVENTION

The present invention relates to compositions and methods for preventing the stinging of marine organisms, such as jellyfish. More specifically, the present invention relates to compositions and methods for inhibiting nematocyst or polar capsule discharge and protecting a subject from nematocyst sting.

BACKGROUND OF THE INVENTION

Swimmers and divers throughout the world are familiar with the stinging organisms of the oceans, such as jellyfish, sea anemone and coral. Jellyfish stings, although seldom fatal, are a major public-health problem. Lotan et al. (1992) Marine Biology 112:237–242; Lotan et al. (1994) Marine Ecology Progress Series 109:59–65. In the summer months, it is estimated that over 500,000 swimmers and divers in the Chesapeake Bay area and 200,00 persons in Florida are stung by jellyfish, mainly by "sea nettles," the common name of Chrysaora quinquecirrha. Burnett et al. (1992) MMI 41(6):509–513. Similarly, between the months of March and August in Florida, one in four bathers are stung and more than 10,000 persons require emergency medical treatment for pruritic eruptions caused by contact with jellyfish larvae known as "sea lice." Tomchik el al. (1993) JAMA 269(13):1669–1672.

The members of the phylum Cnidaria (e.g., jellyfish, sea anemone and coral) and the phylum Myxozoa are all equipped with stinging subcellular organelles known as nematocysts, cnidocysts, or polar capsules. The nematocysts are located in specialized cells (nematocytes) and consist of capsules each containing a condensed tubule with potent toxins and threads. When nematocysts discharge, the tubule penetrates its target organism and releases its toxins. The threads arrayed on the tubule enhance the anchoring and attachment of the nematocyst tubule to its target. Nematocysts are involved in target recognition, toxin delivery, infection and attachment.

All members of the phyla Cnidaria and Myxozoa contain nematocysts of varying sizes, shapes and types Mariscal, pp. 129–178, "Nematocysts" in COELENTERATE BIOLOGY: REVIEWS AND NEW PERSPECTIVES, eds. Muscatine and Lenhoff (Academic Press, New York, 1974). These different types of cnidocysts function in diverse biological roles including capture of prey, toxin delivery, recognition, attachment, adherence and infection. (see, e.g., Tardent (1995); Bioessays 17(4):351–362; Lotan et al. (1995) Nature 375:4A56; Lotan et al. (1996) Expt'l Zool. 275:444–45 1; Lotan (1996) et al., pp. 132–145, "Toxicology and ecology and the Mediterranean jellyfish Rhopileim nomadica" in BIOCHEMICAL ASPECTS OF MARINE PHARMACOLOGY, eds. Lazarovici et al. (Alaken, Inc., Fort Collins, Colo., 199Q; Spaulding (1972) Biol. Bull. 143:440–453; Holstein and Tardent (1984) Science 223:830–833 and Mariscal, supra. Although best known for their stinging capabilities, nematocysts also play a key role in recognition, attachment and infection. For example, parasites from the phylum Myxozoa use nematocysts (polar capsules) to recognize and infect their hosts. El-Matbouli et al. (1995) J. Fish Biol. 46:919–935 and Yokoyama et al. (1995) Diseases Aquatic Organ. 21:7–11.

The main body of the nematocyte cell consists of a dense capsule, the nematocyst, within which is a highly folded eversible tubule. Discharge (eversion) of this tubule is driven by the build up of a high internal hydrostatic pressure of approximately 150 atmospheres within the capsule. The eversion of the internally folded tubule occurs within 3 microseconds at accelerations of up to 40,000×g, one of the most rapid mechanical events in cell biology.

The nematocyte can be sub-divided into 3 morphological compartments with different functional entities: the capsule lumen and wall, the tubule and the sensory organelles. The capsule wall and lumen are the main components involved in developing the driving force for nematocyst discharge. The tension on the inner capsule wall during nematocyst discharge reaches up to 375 MPa. Holstein (1994) Science 265:402–404. The strong capsule wall is highly permeable to water with a pore size of 600 Dalton. Within the resting nematocyst capsule, concentrations of up to 0.5 M of cations such as $Ca^{++}$, $Mg^{++}$ or $K^+$ can be found. (see, e.g., Tardent, supra; Lubbock et al. (1981) PNAS 78(6):3624–3628; Godknecht et al. (1988) Marine Biology 100:83–92; Lubbock and Amos (1981) Nature 290(5806):500–501; Weber (1989) Int. J. Biochem. 184:465–476; Hidaka (1993) Biol. Bull. 184:97–104 and Gerke (1991) Hydrobiologia 216/217: 661–669 for discussions of cations and nematocysts). The anionic counterparts are represented by poly-.gamma.-L-glutamatic acid (PGA) in varying degrees of polymerization. During nematocyst discharge, an extreme increase in internal capsule osmotic pressure occurs due to the influx of water. It has been suggested that the influx of water into the capsule is mediated by an internal release of the cations, such as $Ca^{++}$ in sea anemone or $K^+$ in hydra normally combined with PGA. This osmotic pressure is translated into hydrostatic pressure causing the eruption and then evagination of the tubule from the nematocyst capsule (discharge). After the nematocyst discharge, the internal cation concentration of the capsule is dissolved into the surrounding fluids.

The second compartment of the nematocyst is a highly condensed eversible tubule. This tubule serves the main role in nematocyte biological function, namely, the interaction or delivery of substances from the cnidarian or myxozoan into its target. The tubule, which is 200–850 μm when elongated, is twisted more than a hundred times around its axis and is packed into the 3–10 Jim diameter of the nematocyst. Godknecht & Tardent (1988) Marine Biol. 100:83–92. Hollow barbs, arrayed on the inner surface of the tubule, become everted during discharge and play an important role in the penetration and anchoring of the tubule into its prey. Toxins, contained on the outer surface before discharge, are delivered through the barbs after the nematocyst is anchored. Lotan et al. (1995), supra.

In sum, nematocysts provide an effective method of delivering a substance deep into the target. Because nematocysts are able to penetrate their target so efficiently, it is difficult to remove them or to treat after the toxin has penetrated. Conventionally, nematocyst stings have been treated with antidotes such as steroids, aluminum sulfate/surfactant and antihistamines. Tomchik, supra.

Since post-sting treatments for nematocyst stings are often unsatisfactory, the search for ways to prevent nematocyst discharge has been ongoing. The most often prescribed method of preventing jellyfish stings is to avoid any contact with the nematocysts. Tomchik, supra. However, in the case of microscopic larvae, this often means foregoing all ocean activities during the months of high incidence, (e.g., March through August in Florida). It would, therefore, be useful to have a means for inhibiting nematocyst discharge even when contact does occur.

Australian patent application 67563/94 (WO 94117779) discloses topical hydrodispersion preparations that are reported to be effective in preventing nematocyst discharge as measured by scanning electron microscopy (SEM). The formulations contain inorganic micropigments incorporated into the lipid phase of the hydrodispersion and an optional UV filtering substance and are essentially free of emulsifiers.

Lubbock (1979) *J. Exp. Biol.* 83:283–292 describes how proteinaceous compounds tend to induce a stronger response leading to nematocyst discharge in sea anemones than either polysaccharides or lipids. The authors could determine no simple recognition basis and speculated that the process of nematocyst discharge was complex. Lubbock and Amos, supra, disclose that isolated nematocyst capsules do not discharge in 50 mM $CaCl_2$. The authors report that inhibition of nematocyst discharge occurs only if a solute that cannot rapidly penetrate the capsule wall is used, for example, high molecular weight polyethylene glycol. Thus, calcium in the surrounding environment may stabilize nematocysts because it reduces the differential between the calcium concentration outside and inside the capsule. Normally, the calcium concentration inside the nematocyst capsule is approximately 600 mM. Normal calcium concentration in sea water is around 7 mM, about 100-fold less than inside the capsule. Thus, increasing the calcium concentration outside the capsule to 50 mM reduces the differential to around 10 fold and may be involved in inhibiting nematocyst discharge.

Heeger et al. (1992) *Marine Biology* 113:669–678 tested the ability of three commercially available sunscreen lotions to inhibit jellyfish nematocyst discharge on samples of live human skin. Two of the three lotions were effective at reducing the number of nematocysts discharged. The authors concluded that glycerol and oil components of the lotions could be masking or suppressing the effects of natural stimuli of the skin, although even the lotion which did not inhibit nematocyst discharge contained these substances. Hartwick et al. (1980) *Med. J. Australia* 1:15–20 reported that commercial sting remedies do not inhibit nematocyst discharge.

Water soluble aluminum salts are known to serve as a method for treatment of bites, stings and wounds (Australian patent 475036, 513 983). The mechanisms of the action of aluminum salts in relation to relief of bites or stings is not clear, and it was suggested that the aluminum ion denatures venom, toxins and other stinging substances which may be the pain-causing agents. A composition for treatment of venomous bites and stings was developed by Douglas Henderson (U.S. Pat. No. 2,110,534). This waterproof composition contains concentrations of 13%–56% of aluminum salts and Methyl Eugenol and was found to be effective when applied topically against stinging from Bluebottle (Portuguese Man-o-War). The composition gave limited protection against Box jellyfish (*Chronex fleckeri*) stings.

Santoro et al (1991) *J. Exp. Biol.* 156, 173–185 demonstrated that induction of nematocysts discharge in the Sea anemone is $Ca^{++}$ dependent. Aiptasia Mutabilis acontial filament was incubated in the $Ca^{++}$-free artificial seawater (ASW) and the potential nematocycsts discharge was tested. Exposing the tentacles to several inducers of nematocyst discharge did not result in nematocyst activation. Nematocyst activation was resumed when 10 mM of $Ca^{++}$ was introduced into the ASW medium. For understanding the role of $Ca^{++}$ in nematocyst activation, several $Ca^{++}$ channel inhibitors were applied to the tentacles. It was shown that incubation of sea anemone acontial filament in seawater medium containing 2 mM $LaCl_3$, $CoCl_2$, inactivates nematocyst discharge.

Salleo et al (1994) *J. Exp. Biol.* 187, 201–206 demonstrated that the $Ca^{++}$ channel inhibitor $Gd^{+3}$ applied through a gelatin probe, prevents discharge of nematocyte batteries in the oral arms of *Pelagia nociluca*.

Since nematocyst stings present a major public health problem, especially in the summer months, the search for ways to prevent nematocyst discharge has been ongoing. It would, therefore, be useful to develop efficient methods for inhibiting nematocyst discharge even when contact does occur.

SUMMARY OF THE INVENTION

The present invention provides compositions comprising at least one cation selected from the group consisting of $Ga^{+3}$ and $La^{+3}$ that effectively inhibit the discharge of nematocysts or polar capsules. The compositions described herein are effective at inhibiting nematocyst or polar capsule discharge when applied topically prior to exposure to nematocysts. Thus the present invention provides protection for swimmers, divers and fishermen from nematocysts or polar capsules discharged from stinging marine organisms such as *Cnidaria* and *Myxozoa*.

In one embodiment, the present invention provides a composition for inhibiting the discharge of nematocysts or polar capsules, the composition comprising an effective amount of at least one cation selected from the group consisting of $Ga^{+3}$ and $La^{+3}$ as the active ingredient in a vehicle suitable for topical application.

In another embodiment, the present invention provides a method of inhibiting the discharge of nematocysts or polar capsules, the method comprising the step of applying to the skin of a subject prior to contact with nematocysts or polar capsules a water-proof composition comprising an effective amount of at least one cation selected from the group consisting of $Ga^{+3}$ and $La^{+3}$ as the active ingredient, in a vehicle suitable for topical application, so as to inhibit the discharge of nematocysts or polar capsules.

In another embodiment, the present invention provides a method of preventing *Cnidaria* sting, the method comprising the step of inhibiting the discharge of nematocysts or polar capsules by applying to the skin of a subject prior to contact with nematocysts or polar capsules a water-proof composition comprising an effective amount of at least one cation selected from the group consisting of $Ga^{+3}$ and $La^{+3}$ as the active ingredient, in a vehicle suitable for topical application, so as to inhibit the discharge of nematocysts or polar capsules, thereby preventing *Cnidaria* sting.

In one embodiment, the cation is $Ga^{+3}$, for example in the form of $GaCl_3$. In another embodiment, the cation is $La^{+3}$, for example in the form of $LaCl_3$. In one embodiment, the concentration of the cation is from 1 mM to 500 mM. In another embodiment, the concentration of the cation is from 1 mM to 200 mM. In another embodiment, the concentration of the cation is from 1 mM to 50 mM. In another embodiment, the concentration of the cation is 2 mM. In another embodiment, the concentration of the cation is 5 mM. In another embodiment, the concentration of the cation is 50 mM.

In one embodiment, the vehicle comprises a lipid. In another embodiment, the vehicle comprises a silicone polymer. In another embodiment, the composition further comprises a sunscreen. In another embodiment, the composition is in the form of a skin cream, face cream, lotion, spray or ointment.

In one embodiment, the nematocysts are discharged from a stinging organism selected from the phyla *Cnidaria* and *Myxozoa*. In another embodiment, the stinging marine organism is *Cnidaria* consisting of jellyfish, sea anemone and coral.

During the stinging event the intensity of the sting symptoms is in proportion to the number of nematocysts that have penetrated the skin. This invention demonstrates that *Cnidaria* nematocyst discharge onto human skin can be inhibited with a water-proof composition comprising at least one cation selected from the group consisting of $Ga^{+3}$ and $La^{+3}$ in a vehicle suited for topical application.

BRIEF DESCRIPTION OF THE FIGURES

The present invention will be understood and appreciated more fully from the following detailed description taken in conjunction with the appended drawings.

DETAILED DESCRIPTION OF THE INVENTION

Figure 1:
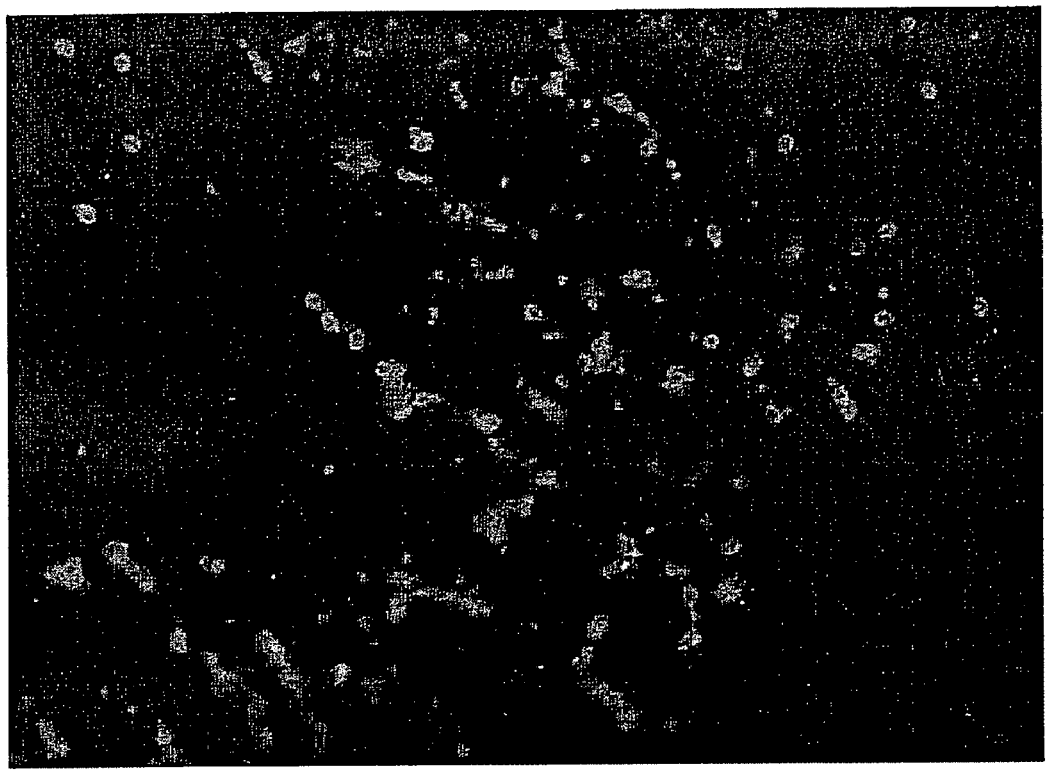
FIG. 1: Immunohistochemical stain of discharge of nematocyst within human skin. Human skin sections were exposed to jellyfish tentacles of *Rhopilema nomadica*. The Jellyfish stinging capsules that penetrated the skin were labeled with specific immunofluorescent antibody goat anti-rabbit FITC. Each dot represents a stinging capsule that has penetrated the skin.

The present invention provides compositions comprising at least one cation selected from the group consisting of $Ga^{+3}$ and $La^{+3}$ that effectively inhibit the discharge of nematocysts or polar capsules. The compositions described herein are effective at inhibiting nematocyst or polar capsule discharge when applied topically prior to exposure to nematocysts. The present invention further provides methods for inhibiting the discharge of nematocysts or polar capsules, comprising applying to the skin of a subject prior to contact with the nematocyst or polar capsule a composition comprising at least one cation selected from the group consisting of $Ga^{+3}$ and $La^{+3}$. Thus, the present invention provides protection for swimmers, divers and fishermen from nematocysts or polar capsules discharged from stinging marine organisms such as *Cnidaria* and *Myxozoa*.

In one embodiment, the present invention provides a composition for inhibiting the discharge of nematocysts or polar capsules, the composition comprising an effective amount of at least one cation selected from the group consisting of $Ga^{+3}$ and $La^{+3}$ as the active ingredient in a vehicle suitable for topical application.

In another embodiment, the present invention provides a method of inhibiting the discharge of nematocysts or polar capsules, the method comprising the step of applying to the skin of a subject prior to contact with nematocysts or polar capsules a water-proof composition comprising an effective amount of at least one cation selected from the group consisting of $Ga^{+3}$ and $La^{+3}$ as the active ingredient, in a vehicle suitable for topical application, so as to inhibit the discharge of nematocysts or polar capsules.

In another embodiment, the present invention provides a method of preventing *Cnidaria* sting, the method comprising the step of inhibiting the discharge of nematocysts or polar capsules by applying to the skin of a subject prior to contact with nematocysts or polar capsules a water-proof composition comprising an effective amount of at least one cation selected from the group consisting of $Ga^{+3}$ and $La^{+3}$ as the active ingredient, in a vehicle suitable for topical application, so as to inhibit the discharge of nematocysts or polar capsules, thereby preventing *Cnidaria* sting.

The term "nematocyst" or "cnidocyst" or "polar capsule" is used in the conventional sense to refer to the subcellular stinging structures found in the nematocytes or cnidocytes. Nematocysts are described in detail in Tardent, supra and Mariscal, supra. These stinging organelles are capable of penetrating, anchoring into and injecting a substance such as a toxin into a target organism.

The terms "nematocyte" or "cnidocyte" or "cnidoblast" are intended to refer to the specialized cells that contain the nematocysts. Non-limiting examples of classes of the phylum *Cnidaria* that possess cnidocytes include, for example, *Hydrozoa, Anthozoa, Myxozoa* and *Scyphozoa*. Examples of jellyfish include, but are not limited to, *Aurelia* sp., *Pelagia* sp., *Chrysaora* sp., *Anthoplaura* sp., *Rhopilema* sp., *Physalia* sp., *Cyanea* sp., *Linuche* sp., *Catostylus* sp., *Carybdea* sp., *Chironex* sp., *Stomolophus* sp., *Rhiozostoma* sp., *Corinactis* sp. and the like.

In one embodiment, the nematocysts are discharged from a stinging organism selected from the phyla *Cnidaria* and *Myxozoa*. In another embodiment, the stinging marine organism is *Cnidaria* consisting of jellyfish, sea anemone and coral.

The term "cation" refers to any positively charged ion. In one embodiment, the cation is a metal cation. In another embodiment, the cation is $Ga^{+3}$. In another embodiment, the cation is $La^{+3}$. The cation can be from any suitable cation source. The term "cation source" refers to any substance which is capable of supplying positively charged ions, such as salts. Any salt of the cation may be used in the present invention. Nonlimiting examples are halo salts such as chlorides, bromides and iodides Thus, in one embodiment, the salt is a chloride salt. In another embodiment, the salt is $LaCl_3$. In another embodiment, the salt is $GaCl_3$. It will be appreciated by one skilled in the art that other salts are also suitable, such as $Co^{+2}$ and $Cd^{+2}$ salts, for example $CoCl_2$ and $CdCl_2$. These cations can be obtained from various commercial vendors.

The term "effective amount" refers to an amount sufficient to effect beneficial or desired results. For purposes of this invention, an effective amount of a cation is an amount sufficient to inhibit, limit, repress, palliate or prevent the discharge of nematocysts or polar capsule and/or to inhibit, limit, repress, palliate or prevent *Cnidaria* sting. In one embodiment, the concentration of the cation is from 1 mM to 500 mM. In another embodiment, the concentration of the cation is from 1 mM to 200 mM. In another embodiment, the concentration of the cation is from 1 mM to 50 mM. In another embodiment, the concentration of the cation is 2 mM. In another embodiment, the concentration of the cation is 5 mM. In another embodiment, the concentration of the cation is 50 mM.

The compositions comprising $La^{+3}$ and/or $Ga^{+3}$ are incorporated into various formulations. Such formulations include but are not limited to: topical formulations, emulsions, sprays, liquid dispersions, solutions, skin creams, face creams, lotions or ointments. Such compositions may contain emulsifiers, water, emollients, dry-feel agents, water-proofing agents, preservatives, antioxidants, anti-foaming agents and fragrances as well as any other class of materials whose presence may be desirable, known to those skilled in the art.

Topical Formulations

In one embodiment, the compositions and/or formulations described herein are topical formulations which are suited to be topically applied to a subject. Thus, the compositions described herein comprise a vehicle suitable for topical application. Topical formulations containing compositions within the present invention create physical barriers to minimize skin stimulant secretion and are, themselves, not stimulants. Formulations should be water-proof so as to be useful for swimmers and divers. Examples of vehicles suitable for topical application include, but are not limited to, dextran, dextran sulfate, agarose, phosphatidyl ethanolamine, cholesterol, cholesterol palmitate, palmitic acid, oleic acid, lysolecitin, phosphatidyl choline, phosphatidyl serine, phosphatidyl inositol, squalene, phenyl trimethicone, stearic acid, propylene glycol sterate, petrolatum, stearoxytrimethyl-silane, stearyl alcohol. Other vehicles are known to those skilled in the art. Silicone polymers are preferred as they provide good barriers, are water-proof and do not stimulate nematocyst discharge.

In one embodiment, the compositions of the present invention are incorporated in a vehicle that comprises a lipid. A wide variety of lipid type materials and mixtures of materials are suitable for use as the vehicle in the compositions of the present invention.

Emulsions/Emulsifiers

An emulsion is a mixture of two immiscible liquids, i.e. liquids that are not mutually soluble, that are mechanically agitated and shaken so thoroughly together that one liquid forms drops in the other one, giving the mixture the appearance of a homogeneous liquid. If the emulsifier is added to the two immiscible liquids, one of them becomes continuous and the other one remains in droplet form. As used herein in reference to water-in-oil emulsifiers, the term "HLB value" means the hydrophilic-lipophilic balance. The HLB value has been used by those skilled in the emulsion art for selecting emulsifiers useful for preparing water-in-oil emulsions. See U.S. Pat. No. 4,177,259 and references cited therein.

An oil-in-water (o/w) emulsion is a mixture in which oil droplets (the discontinuous phase) are dispersed in water (a continuous aqueous phase). A water-in-oil (w/o) emulsion is a mixture in which water droplets (the discontinuous phase) are dispersed in oil (a continuous oil phase). The type of emulsion, oil-in-water (o/w) or water-in-oil (w/o), is determined by the volume ratio of the two liquids, provided the ratio is sufficiently high. For example, with 5% water and 95% oil (an o/w phase ratio of 19), the emulsion likely will become w/o. For moderate ratios (<3), the type of emulsion is decided by several factors, such as order of addition or type of emulsifier. One liquid slowly added to a second liquid with agitation usually results in the second liquid being the continuous phase. Another factor is preferred solubility of the emulsifier, the phase in which the emulsifier is soluble most probably is continuous.

More complex emulsions, such as double emulsions, are formed when an emulsion is dispersed in a continuous phase. For example, in an oil-in-water-in-oil (o/w/o) emulsion, the water in a continuous water phase containing dispersed oil droplets, which are themselves dispersed in a continuous oil phase. Similarly, in a water-in-oil-in water emulsion, the oil in a continuous phase containing dispersed water droplets, which are themselves dispersed in a continuous water phase. These more complex emulsions find use as a system for slow delivery, extraction, etc.

An emulsifier (a stabilizing compound) is an agent used to assist in the production of an emulsion. Typically, emulsifiers are molecules with non-polar and polar parts that are able to reside at the interface of the two immiscible liquids. Water may be used as a diluent or can be the internal (discontinuous) or external (discontinuous) phase of an emulsion system.

An emollient is an oil-containing agent which helps to smooth and soften the skin, and may also reduce its roughness, cracking or irritation. Typical suitable cosmetic emollients include mineral, oil, having a viscosity in the range of 50 to 500 SUS, lanolin oil, coconut oil, cocoa butter, olive oil, almond oil, macadamia nut oil, aloe extract, jojoba oil, safflower oil, corn oil, liquid lanolin, cottonseed oil and peanut oil. Other typical suitable cosmetic emollients include Purcellin oil, perhydrosqualene, castor oil, polybutene, odorless mineral spirits, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate. Other typical suitable cosmetic emollients that are solids or semi-solids at ambient temperatures may be used if admixed with mineral oil or extra heavy mineral oil in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. Typical suitable emollients include esters of a straight or branched-chain $C_{10}$–$C_{16}$ alcohol and a straight or branched chain $C_4$–$C_{20}$ mono- and dicarboxylic acids include the straight and branched chain monocarboxylic acids substituted by hydroxy or double bonds including monocarboxylic acids such as: butanoic, pentanoic, 2-methyl- and 3-methyl-pentanoic, 2,2-dimethylpropanoic, hexanoic, 2-methyl-, 3-methyl-, and 4-methyl-, 5-methyl- and 6-methyl-heptanoic, 2-ethylhexanoic, octanoic (caprylic), 2-methyl-, 3-methyl-, 4-methyl-, 5-methyl-, 6-methyl-, 7-methyl- and 8-methyl-nonanoic, 3,3,5-trimethylexanoic (isonanomic), decanoic (caproic), 2-methyl-, 3-methyl-, 4-methyl-, 5-methyl-, 6-methyl-, 7-methyl-, 8-methyl-, 9-methyldecanoic, undecanoic, dodecanoic (lauric), dineopentylacetic, methyl-t-butyineopentylacetic, tridecanoic, tetradecanoic (myristic), pentadecanoic, hexadecanoic (palmitic), heptadecanoic (margaric), octadecanoic (stearic), hydroxystearic 16-methylheptadecanoic (isistearic), double bond subsituted (unsaturated) carboxylic acids such as oleic (cis-9-octadecenoic), linoleic (cis, cis-9,12-octadecadienoic) and linolenic cis,cis,cis-9,12,15-octadecadienoic acid), nonadecanioc and $CH_3(CH)_{18}$ $CO2H$. Typical suitable $C_4$–$C_{20}$ dicarboxylic acids include dicarboxylic acids of the formula $(CH_2)_n(CO2H)_2$ wherein n is 2 to 18 including succinic (n=2), glutaric (n=3), adipic (n=4), pimelic (n=5), suberic (n=6), azelaic (n=7), sebacic (n=8) as well as the C12, C16 and C19 members such as Brassilic (C13), thapsic (C16) and nonadecance-1,19-dicarboxylic acid. In one embodiment, the carboxylic acid is succinic acid. In another embodiment, the carboxylic acid is adipic acid.

Typically suitable tri lower alkyl substituted benzoic acids include trimethylbenzoic acids, such as 1,1,3-trimthylbenzoic acid, 1,2,4-trimethyl-benzoic acid (trimellitic acid), and 1,3,5-trimethylbenzoic acid (trimesic acid). (The preferred tri (lower alkyl) benzoic acid is trimellitic acid. Preferred esters of $C_4$ to $C_{20}$ monocarboxylic acids and straight and branched chain $C_{10}$–$C_{16}$ alcohols include tridecyl neopentonate, isotridecyl isononanoate, isodecyl neopentonate, isodecyl hydroxystearate, isodecyl laurate, isodecyl myristate, isodecyl oleate, isodecyl palmitate, decyl oleate, and isocetyl palmitate (isohexadecyl hexadecanoate) and iso-hexadecyl isodecanoate (14-methylpentadecyl-8-methyinonanoate). The preferred ester of straight and branched-chain $C_{10}$–$C_{16}$ alcohols and $C_4$–$C_{20}$ dicarboxylic acids is decyl succinate. In one embodiment, the esters are esters of straight and branched-chain $C_{10}$–$C_{16}$ esters of tri(loweralkyl) substituted benzoic acids are the decyl, isodecyl, isotridecyl and tridecyl esters of trimethylbenzoic acids for example trimellitic acid; tridecyl trimellitate.

The emollient can be a mixture of tridecyltrimellitate and tridecyl stearate or a mixture of tridecyl trimellitate, tridecyl stearate, neopentyl glycol dicaprylate and neopentyl dicaprate such as is available from Lipo Chemicals Inc., Patterson, J. J. under the tradename Lipovol MOS-70. The emollient component can optionally be included in the sunscreen composition in an amount ranging from about 10 to about 50 weight percent, for example about 20 to about 40 percent.

Sunscreens

Optionally, the compositions described herein may contain a known sunscreen. Such sunscreens are also known to those skilled in the art. Preferably, the sunscreens contain at least one UVA filter and at least one UVB filter. Oil-soluble UVB products include 3-benzylidenecamphor derivatives, 4-aminobenzoic acid derivatives, esters of cinnamic acid, derivatives of benzophenone, esters of benzylidenemalonic acid. Water soluble UVA filters include salts of 2-phenylbenzimidazole-5-sulphonic acid, sulphonic acid derivatives of benzophenones and sulphonic acid derivatives of 3-benzylidenecamphor. Effective amounts of sunscreens will be known to those of skill in the art. Preferably, sunscreens will comprise between about 0.1% and 10% by weight of the total preparation. Typical sunscreen active ingredients include trade names of para-aminobenzoic acid up to about 15 weight percent or from about 5 to 15% in admixture with other sunscreen actives; cinoxate up to about 3 weight percent or about 1 to 3% in admixture; diethanolamine methoxycinnamate up to 10 weight percent or about 8 to 10% in admixture; digalloyl trioleate up to 5 weight percent or about 2 to 5% in admixture; dioxybenzone up to 3 weight percent alone or in admixture; ethyl 4-[bis(hydroxypropyl)] aminobenzoate up to 5 weight percent or about 1 to 5% in admixture; glyceryl aminobenzoate up to 3 weight percent or about 2 to 3% in admixture; homosalate up to 15 weight percent or about 4 to 15% in admixture; lawsone up to 0.25 weight percent with dihydroxyacetone up to 3 weight percent; menthyl anthranilate up to 5 weight percent or about 3 to 5% in admixture; octocrylene up to 10 weight percent or 7 to about 10% in admixture; octyl methoxycinnamate up to 7.5 weight percent or about 2 to 7.5% in admixture; octyl salicylate up to 5 weight percent or about 3 to 5% in admixture; oxybenzone up to 6 weight percent or about 2 to 6% in admixture; padimate up to 8 weight percent or about 1.4 to 8% in admixture; phenylbenzimidazole sulfonic acid up to 4 weight percent or about 1 to about 4% in admixture; red veterinary petrolatum up to 95 percent or about 30 to 95% in admixture; sulisobenzone up to 10 weight percent or about 5 to 10% in admixture; titanium dioxide up to 25 weight percent or about 2 to 25% in admixture; and trolamine salicylate up to 12 weight percent or about 5 to 12% in admixture. Other suitable sunscreens include Ethylhexyl (Octyl) Salicylate, Ethylhexyl (Octyl) Salicylate, Methylbenzylidene Camphor, Octocrylene, Bultyl Methoxydibenzoyl methane, Ethylhexyl (Octyl) Methoxycinnamate.

Typical suitable UV-B type sunscreening active ingredients include octyl para-methoxycinnamate available from Givaudan Corporation, Clifton, N.J., under the trade name of Parsol MCX and Parsol 1789, usually present in the range of about 1.5 to about 7.5 weight %, and octyl salicylate available from Harmann and Riemer, Springfield, N.J., 07081, usually in the range of about 3 to about 5 weight %, of the total sunscreen composition or emulsion. The amount of UV-B type sunscreening active ingredients should be sufficient to give an SPF of at least 2 to 15. A typical suitable UV-A type sunscreening active ingredient include benzophenone-3, usually in the range of about 0.5 to about 6 weight %. Such active can be obtained from Rhone-Poulenc, Atlanta, Ga. Sunscreen emulsions containing mixtures of UV-B and UV-A type sunscreen actives should be sufficient to provide an SPF of 4 to 50.

A dry-feel modifier is an agent that gives a sunscreen a "dry feel" upon drying, and may reduce sunscreen migration and can include silazane treated silica, precipitated silica, fumed silica or mixtures thereof. The dry-feel modifier can optionally be included in the sunscreen composition in amounts ranging from about 0.1 to about five weight percent, preferably from about 0.3 to about 1.5%.

Water-Proof Compositions

A waterproofing agent is a material added to the composition to assist in retaining the sunscreen active ingredients on the skin. Typical suitable waterproofing agents for sunscreen raw materials include copolymers derived from polymerization of octadecene-1 and maleic anhydride in accordance with the published procedures such as those in U.S. Pat. No. 3,860,700 and Reissue No. 28,475. In one embodiment, the waterproofing agent is a copolymer commercially available from Chevron Chemicals Co. under the trade name, PA-18 polyanhydride resin. The term "water-proof compositions" means that the waterproofing agent(s) is applied in amounts effective to allow the sunscreen to remain on the skin after exposure to circulating water for at least 80 minutes using the procedures described in "Sunscreen Drug Products for OTC Human Use", Federal Register, Vol. 43, Aug. 25, 1978, Part 2, pages 38206–38269. The waterproofing agent can optionally be included in the sunscreen composition in an amount ranging from about 0.01 to about 10.0 weight percent, preferably about 1.0 to about 10.0 percent.

Other Additives

In one embodiment, the compositions of the present invention further comprise an antimicrobial preservative. An antimicrobial preservative is a substance or preparation that destroys, prevents or inhibits the multiplication/growth of microorganisms in the sunscreen composition and may offer protection from oxidation. Preservatives are used to make aqueous products self-sterilizing. This is done to prevent microorganisms that may be in the product from growing during manufacturing and distribution of the product and during use by consumers who may inadvertently contaminate the product during normal use. Typical preservatives include the lower alkyl esters of para-hydroxybenzoates (parabens) especially, methyl paraben, isobutyl paraben and mixtures thereof, and benzoic acid. The antimicrobial preservative can optionally be included in the sunscreen composition in an amount ranging from about 0.05 to about one percent, preferably about 0.2 to about 0.5 percent. One exemplary preservative is Germaben 11, trade name of Sutton Labs, Chatham, N.J.

In one embodiment, the compositions of the present invention further comprise an antioxidant. An antioxidant is a natural or synthetic substance added to the sunscreen to prevent or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA)(usually as a mixture of orthos and meta isomers), butylated hydroxytoluene (BHT) and nordihydroguaiaretic acid. The antioxidant can optionally be included in the sunscreen composition in an amount ranging from about 0.02 to about 1.0 weight percent, preferably about 0.05 to about 0.1 percent.

Fragrances are aromatic compounds that can impart an aesthetically pleasing aroma to the sunscreen composition and may also be added. Typical fragrances include aromatic materials extracted from botanical sources (i.e. rose petals, gardenia blossoms, jasmine flowers, etc.), which can be used alone or in any combination to create essential oils. Alternatively, alcoholic extracts may be prepared for compounding fragrances. The fragrance can optionally be included in the sunscreen composition in an amount ranging from about 0.01 to about 5.0 weight percent, preferably about 0.1 to about 2.0 percent. Definitions and suppliers of the ingredients used in the following illustrative examples may be found in the CTFA Cosmetic Ingredient Dictionary, published by the Cosmetic, Toiletry and Fragrance Association, Inc., 1110 Vermont Avenue, NW, Wash. D.C. 20005, Third Edition 1982. All proportions are by percent weight.

Further, this invention provides additional agents and/or compounds that are antibacterial metal salts. salts of aluminum, zirconium, zinc, silver, gold, copper, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof. Preferred antimicrobial agents for use herein are the broad spectrum actives selected from the group consisting of Triclosan, Triclocarban, Octopirox, PCMX, ZPT, natural essential oils and their key ingredients, and mixtures thereof. The most preferred antimicrobial active for use in the present invention is Triclosane.

In one embodiment, lipophilic skin-moisturizing agents are included in the compositions herein in an amount ranging from about 0.1% to about 30%, preferably from about 1% to about 30% more preferably from about 3% to about 25%, most preferably from about 5% to about 25% of the composition. In one embodiment, the lipophilic skin-conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. No. 3,600,186 to Mattson, Issued Aug. 17, 1971, and U.S. Pat. No. 4,005,195 and 4,005,196 to Jandacek et al., both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989, and U.S Pat. Nos. 5,306,514, 5,306,516 and 5,306,515 to Letton, all three issued Apr. 26, 1994, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof. Fatty acids, fatty acid soaps and water soluble polyols are specifically excluded from our definition of a lipophilic skin-moisturizing agent.

Hydrocarbon oils and waxes may also be added to the compositions of the present invention. Some examples are petrolatum, mineral oil microcrystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin-moisturizing agent in the compositions herein.

The following examples are intended to illustrate but not to limit the subject invention.

Experimental Details Section

EXAMPLE 1

Inhibition of Nematocyst Discharge into Human Skin Using $LaCl_3$

To test the ability of Lanthanum Chloride to inhibit nematocyst discharge, a test using human skin was performed as described herein.

1. Preparation of Skin Samples

Normal human skin was obtained from neonatal elective circumcision. The skin was immediately placed into sterile phosphate buffered saline (PBS) containing antibiotic/antimycotic. The tissue was frozen and embedded in Tissue-TekTM. It was then sectioned into 50 μm sections using a cryostat. The sections were attached to superfrost/plus microscope slide (Fisherbrand) and maintained at 20° C. until time of use. All sections were examined to ensure that they were perpendicular to the plane of the epidermis, exposing cross-sections of epidiermis, dermis and subcutaneos tissue.

2. Immunoassay to Detect Nematocyst Discharge

For immunoassay tests to detect cnidaria stinging level of human skin, a polyclonal antibody specific for nematocyst toxin was prepared, as described in Lotan et al (1996).

Briefly, the HPLC fraction containing the toxin phospholipase A2 from the jellyfish *Rhopilema nomadica* was isolated and injected into rabbits as described in Vaitukaitis, pp. 46–52, "Immunochemical Techniques, Part B," in Methods in enzymology, vol. 73, ed. Larson & Vunkis (academic Press, New York, 1981). Serum was collected from the rabbits after two injections, and the presence of antibody against the jellyfish toxin was examined on immunoblots.

The slides prepared and frozen as described above were thawed at room temperature. The slides were submersed in sea water and then attached to jellyfish or sea anemone tentacles for 10 seconds. The tentacles were detached, the slide washed with PBS, and blocked using 5% Fetal Bovine Serum, and 0.1% Triton X100 in PBS (blocking solution). All washing incubation steps were conducted on a tilting shaker at room temperature. The slides were incubated at 10 ml of block solution containing a 1:2, 500 dilution of the anti-toxin antibody for one hour. After incubation, the slide were washed five times for five minutes each wash with 100 mL of 0.1% TritonX100 in PBS (Wash solution). The slides were then incubated in 10 mL blocking solution containing a second antibody, Goat anti rabbit FITC (Fluorescent marker) for 30 minutes. After incubation, the slides were washed five times for five minutes each wash with wash solution. The excess PBS was removed by shaking the slides. One drop of 10% glycerol was added to each slide and the slides were covered with glass coverslips. The slides were observed under a conventional light microscope or under an ultraviolet (UV) microscope at least at 200× magnification (FIG. 1).

3. Preparation of Ointment Base for Testing Inhibitory Effect of $LaCl_3$ as a Skin Protectant Against *Cnidarians* Stings.

To test the effect of $LaCl_3$ as a sting protectant against jellyfish sting the basic ointments containing various Lanthanum Chloride concentration were prepared as described Table 1 below:

TABLE 1

| Phase | | Control lotion | 2 mM $LaCl_3$ | 5 mM $LaCl_3$ | 50 mM $LaCl_3$ |
|---|---|---|---|---|---|
| A | MINERAL OIL | 5 | 5 | 5 | 5 |
| A | Cetyl dimethicone | 2 | 2 | 2 | 2 |
| A | Castor oil | 0.25 | 0.25 | 0.25 | 0.25 |
| A | Cerazin wax | 0.5 | 0.5 | 0.5 | 0.5 |
| A | Laurylmethicone Copolyol | 1.5 | 1.5 | 1.5 | 1.5 |
| A | Stearyl Dimethicone | 0.5 | 0.5 | 0.5 | 0.5 |
| B | Cyclometicone | 13 | 13 | 13 | 13 |
| C | H2O | 75.5 | 75.5 | 75.5 | 75.5 |
|   | NaCl2 | 1 |  | 1 | 1 |
|   | Lanthanum Chloride | — | 0.8 | 2 | 20 |
| D | GERMABEN II | 0.5 | 0.5 | 0.5 | 0.5 |
|   |   | 100 | 100 | 100 | 100 |

Preparation of the basic ointments was carried out according to the following protocol:
1. Combine Phase A and heat to 85° C.;
2. Cool to 60° C.;
3. Add Phase B;
4. Under slow stirring add Phase C;
5. Cool to 40° C.;
6. Add phase D; and
7. Homogenize.

4. Inhibition of Nematocyst Discharge into Human Skin Samples Using an Ointment Containing $LaCl_3$ To monitor the influence of 2 mM, 5 mM and 50 mM $LaCl_3$ and the ointment base on nematocyst discharge into human skin, the jellyfish *Rhopilema nomadica* was used.

Twelve sections of human skin samples were tested in each experiment. The sections were marked and lotion with ointment bases and ointment containing $LaCl_3$. The samples were submersed in seawater and then attached to jellyfish tentacles for 10 seconds. The number of nematocysts that penetrated the skin was determined using immunohistochemical analysis.

Figure 2:
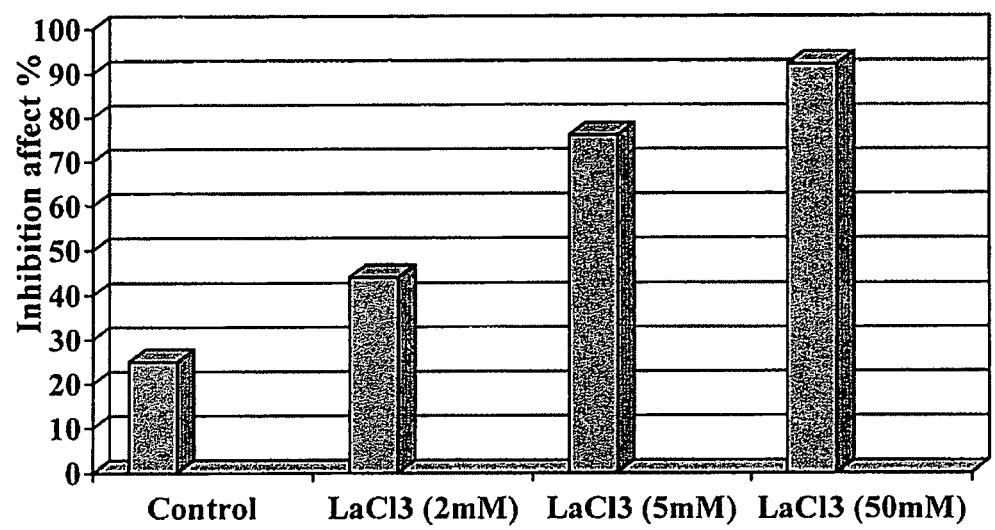
FIG. 2: Effect of 2 mM, 5 mM and 50 mM $LaCl_3$ on the skin of human subjects after a 10 second exposure of direct contact with jellyfish tentacles from *Ropilema*.

As shown in FIG. 2, 2 mM $LaCl_3$ inhibited nematocyst penetration by 44%. Using 5 mM of $LaCl_3$ in the ointment generated 76% reduction in the sting while the addition of 50 mM $LaCl_3$ to the lotion reduced the sting by 92%. This result indicates that $LaCl_3$ in concentration of 50 mM can be effective in certain ointment in inhibition of jellyfish sting.

EXAMPLE 2

Water Proof of Ointment

The ability of the ointment to store the $LaCl_3$ in ocean seawater (i.e. a water-resistant or water-proof formulation) is important for providing bathers with protection against jellyfish sting during prolong water activity. Lanthanum Chloride is a highly soluble molecule and thus Applicants developed a waterproof formulation that is shown to provide $LaCl_3$ waterproof conditions for more than 2 (two) hour.

To determine the water resistance of an ointment containing 50 mM $LaCl_3$, prepared according the above-described conditions, three squares (10×10 CM) of virgin wool, keratin protein that is used as a substrate to approximate human skin, were used. Each square of wool was treated with 1-gram of ointment containing 50 mM $LaCl_3$. After 20 minutes of drying at room temperature, the squares of wool were immersed in one liter of seawater and agitated (80 RPM) for 30 minutes, 60 minutes, or 120 minutes. The ointment was extracted separately from each square of wool with 50 ml 1% Tritox100 under boiling. The Lanthanum chloride concentration of each sample of extracted ointment was monitored with the use of atomic absorption.

The results show that 90% of the 50 mM $LaCl_3$ was retained in the ointment after 30 minuets of water submersion, 77% of the Lanthanum remains after 60 minutes and 70% of the $LaCl_3$ was left after 120 minutes. These results indicate that the ointment can provide a $LaCl_3$ waterproof environment and can be thus used to protect bathers against jellyfish sting during water activity.

What is claimed is:

1. A method of inhibiting the discharge of nematocysts or polar capsules into the skin of a subject, said method comprising the step of applying to the skin of a subject prior to contact with nematocysts or polar capsules a water-proof composition comprising an effective amount of $La^{+3}$ as the active ingredient, in a vehicle suitable for topical application, so as to inhibit the discharge of nematocysts or polar capsules.

2. The method according to claim 1, wherein the $La^{+3}$ is $LaCl_3$.

3. The method according to claim 1, wherein the vehicle comprises a lipid.

4. The method according to claim 1, wherein the vehicle comprises a silicone polymer.

5. The method according to claim 1, wherein the composition further comprises a sunscreen.

6. The method according to claim 1, wherein the composition is in the form of a skin cream, face cream, lotion, spray or ointment.

7. The method according to claim 1, wherein the nematocysts are discharged from a stinging organism selected from the phylum consisting of *Cnidaria* and *Myxozoa*.

8. The method according to claim 7, wherein the stinging marine organism is *Cnidaria* consisting of jellyfish, sea anemone and coral.

9. The method according to claim 1, wherein the concentration of the cation is from 1 mM to 500 mM.

10. The method according to claim 1, wherein the concentration of the cation is from 1 mM to 200 mM.

11. The method according to claim 1, wherein the concentration of the cation is from 1 mM to 50 mM.

12. The method according to claim 1, wherein the concentration of the cation is 2 mM.

13. The method according to claim 1, wherein the concentration of the cation is 5 mM.

14. The method according to claim 1, wherein the concentration of the cation is 50 mM.

15. A method of preventing *Cnidaria* stinging of a subject, said method comprising the step of inhibiting the discharge of nematocysts or polar capsules by applying to the skin of a subject prior to contact with nematocysts or polar capsules a water-proof composition comprising an effective amount of $La^{+3}$ as the active ingredient, in a vehicle suitable for topical application, so as to inhibit the discharge of nematocysts or polar capsules, thereby preventing *Cnidaria* stinging of a subject.

16. The method according to claim 15, wherein the $La^{+3}$ is $LaCl_3$.

17. The method according to claim 15, wherein the vehicle comprises a lipid.

18. The method according to claim 15, wherein the vehicle comprises a silicone polymer.

19. The method according to claim 15, wherein the composition further comprises a sunscreen.

20. The method according to claim 15, wherein the composition is in the form of a skin cream, face cream, lotion, spray or ointment.

21. The method according to claim 15, wherein the *Cnidaria* consist of jellyfish, sea anemone and coral.

22. The method according to claim 15, wherein the concentration of the cation is from 1 mM to 500 mM.

23. The method according to claim 15, wherein the concentration of the cation is from 1 mM to 200 mM.

24. The method according to claim 15, wherein the concentration of the cation is from 1 mM to 50 mM.

25. The method according to claim 15, wherein the concentration of the cation is 2 mM.

26. The method according to claim 15, wherein the concentration of the cation is 5 mM.

27. The method according to claim 15, wherein the concentration of the cation is 50 mM.

* * * * *